United States Patent
Lu et al.

(10) Patent No.: US 10,456,105 B2
(45) Date of Patent: Oct. 29, 2019

(54) SYSTEMS AND METHODS WITH A SWELLABLE MATERIAL DISPOSED OVER A TRANSDUCER OF AN ULTRASOUND IMAGING SYSTEM

(71) Applicant: Boston Scientific SciMed, Inc., Maple Grove, MN (US)

(72) Inventors: Xin Lu, Palo Alto, CA (US); Eric Elliott, San Francisco, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 788 days.

(21) Appl. No.: 15/145,441

(22) Filed: May 3, 2016

(65) Prior Publication Data

US 2016/0324502 A1    Nov. 10, 2016

Related U.S. Application Data

(60) Provisional application No. 62/157,385, filed on May 5, 2015.

(51) Int. Cl.
*A61B 8/12* (2006.01)
*A61B 8/00* (2006.01)

(52) U.S. Cl.
CPC .............. *A61B 8/12* (2013.01); *A61B 8/4281* (2013.01); *A61B 8/445* (2013.01); *A61B 8/4483* (2013.01)

(58) Field of Classification Search
None
See application file for complete search history.

(56) References Cited

U.S. PATENT DOCUMENTS

| | | | |
|---|---|---|---|
| 4,817,015 | A | 3/1989 | Insana et al. |
| 4,858,124 | A | 8/1989 | Lizzi et al. |

(Continued)

FOREIGN PATENT DOCUMENTS

| | | |
|---|---|---|
| EP | 1239774 A2 | 9/2002 |
| EP | 1739593 A1 | 1/2007 |

(Continued)

OTHER PUBLICATIONS

International Search Report & Written Opinion, International Application No. PCT/US2012/030707 dated Jun. 5, 2012, 11 pages.

(Continued)

*Primary Examiner* — Jason T Yen
(74) *Attorney, Agent, or Firm* — Lowe Graham Jones PLLC; Bruce E. Black

(57) ABSTRACT

A catheter assembly for an ultrasound system includes an elongated catheter for insertion into the cardiovascular system of a patient. The catheter includes a sheath that defines a lumen extending along the sheath. The catheter assembly also includes an imaging core for inserting into the lumen of the catheter. The imaging core includes an elongated, rotatable driveshaft and an imaging device coupled to the distal end of the driveshaft with rotation of the driveshaft causing a corresponding rotation of the imaging device. The imaging device includes at least one transducer for transforming applied electrical signals to acoustic signals and also for transforming received echo signals to electrical signals. The imaging core further includes a swellable material disposed on at least the at least one transducer and configured and arranged to rotate with rotation of the driveshaft and to swell upon exposure to a fluid.

15 Claims, 5 Drawing Sheets

(56) References Cited

U.S. PATENT DOCUMENTS

| | | | |
|---|---|---|---|
| 4,905,700 A | 3/1990 | Wokalek et al. | |
| 5,081,993 A | 1/1992 | Kitney et al. | |
| 5,115,814 A * | 5/1992 | Griffith | A61B 5/06 600/439 |
| 5,375,602 A | 12/1994 | Lancee et al. | |
| 5,400,785 A * | 3/1995 | Crowley | A61B 8/12 428/400 |
| 5,406,951 A * | 4/1995 | ten Hoff | A61B 8/12 600/463 |
| 5,497,770 A | 3/1996 | Morcos et al. | |
| 6,019,724 A | 2/2000 | Gronningsaeter et al. | |
| 6,192,360 B1 | 2/2001 | Dumais et al. | |
| 6,200,266 B1 | 3/2001 | Vince et al. | |
| 6,238,342 B1 | 5/2001 | Feleppa et al. | |
| 6,669,662 B1 * | 12/2003 | Webler | A61B 8/12 604/151 |
| 6,945,938 B2 | 9/2005 | Grunwald | |
| 7,037,271 B2 | 5/2006 | Crowley | |
| 7,074,188 B2 | 7/2006 | Nair et al. | |
| 7,175,597 B2 | 2/2007 | Vince et al. | |
| 7,245,789 B2 | 7/2007 | Bates et al. | |
| 7,246,959 B2 | 7/2007 | Nakatani | |
| 7,306,561 B2 | 12/2007 | Sathyanarayana | |
| 7,447,388 B2 | 11/2008 | Bates et al. | |
| 7,622,853 B2 | 11/2009 | Rehrig et al. | |
| 7,672,706 B2 | 3/2010 | Sathyanarayana | |
| 7,729,533 B2 | 6/2010 | Sathyanarayana | |
| 7,892,175 B2 | 2/2011 | Wakabayashi et al. | |
| 2003/0220556 A1 | 11/2003 | Porat et al. | |
| 2004/0067000 A1 | 4/2004 | Bates et al. | |
| 2004/0146201 A1 | 7/2004 | Sathyanarayana | |
| 2004/0254463 A1 | 12/2004 | Lehman | |
| 2005/0043614 A1 | 2/2005 | Huizenga et al. | |
| 2005/0065426 A1 | 3/2005 | Porat et al. | |
| 2005/0154315 A1 | 7/2005 | Nair et al. | |
| 2005/0203410 A1 | 9/2005 | Jenkins | |
| 2005/0228254 A1 | 10/2005 | Torp et al. | |
| 2005/0249391 A1 | 11/2005 | Kimmel et al. | |
| 2005/0251116 A1 | 11/2005 | Steinke et al. | |
| 2006/0041199 A1 | 2/2006 | Elmaleh et al. | |
| 2006/0056703 A1 | 3/2006 | Sathyanarayana | |
| 2006/0058622 A1 | 3/2006 | Tearney | |
| 2006/0058653 A1 | 3/2006 | Sathyanarayana | |
| 2006/0100522 A1 | 5/2006 | Yuan | |
| 2006/0106320 A1 | 5/2006 | Barbato | |
| 2006/0120608 A1 | 6/2006 | Luo et al. | |
| 2006/0173350 A1 | 8/2006 | Yuan | |
| 2006/0222221 A1 | 10/2006 | Sathyanarayana | |
| 2006/0235286 A1 | 10/2006 | Stone et al. | |
| 2006/0253028 A1 | 11/2006 | Lam | |
| 2006/0271040 A1 | 11/2006 | Horne et al. | |
| 2006/0277998 A1 | 12/2006 | Masotti | |
| 2007/0003116 A1 | 1/2007 | Yuan et al. | |
| 2007/0005356 A1 | 1/2007 | Perronnin | |
| 2007/0016054 A1 | 1/2007 | Cao | |
| 2007/0038111 A1 | 2/2007 | Rehig et al. | |
| 2007/0049827 A1 | 3/2007 | Donaldson | |
| 2007/0055153 A1 | 3/2007 | Simopoulos et al. | |
| 2007/0078500 A1 | 4/2007 | Ryan et al. | |
| 2007/0083111 A1 | 4/2007 | Hossack et al. | |
| 2007/0100239 A1 | 5/2007 | Nair et al. | |
| 2007/0127789 A1 | 6/2007 | Hoppel et al. | |
| 2007/0133925 A1 | 6/2007 | Bates et al. | |
| 2007/0160275 A1 | 7/2007 | Sathyanarayana | |
| 2007/0165920 A1 | 7/2007 | Gering et al. | |
| 2007/0237371 A1 | 10/2007 | Zhu et al. | |
| 2007/0260141 A1 | 11/2007 | Margolis et al. | |
| 2007/0265521 A1 | 11/2007 | Redel et al. | |
| 2007/0282202 A1 | 12/2007 | Maurice et al. | |
| 2007/0299343 A1 | 12/2007 | Waters | |
| 2008/0039830 A1 | 2/2008 | Munger et al. | |
| 2008/0063265 A1 | 3/2008 | Sathyanarayana | |
| 2008/0125772 A1 | 5/2008 | Kleyman | |
| 2008/0234582 A1 | 9/2008 | Nair et al. | |
| 2008/0312673 A1 | 12/2008 | Viswanathan et al. | |
| 2009/0059727 A1 | 3/2009 | Bates et al. | |
| 2009/0105579 A1 | 4/2009 | Garibaldi | |
| 2009/0137952 A1 | 5/2009 | Ramamurthy et al. | |
| 2009/0264769 A1 | 10/2009 | Sadaka | |
| 2009/0299195 A1 | 12/2009 | Muller et al. | |
| 2010/0249599 A1 * | 9/2010 | Hastings | A61B 5/02007 600/459 |
| 2010/0249603 A1 | 9/2010 | Hastings et al. | |
| 2011/0009734 A1 * | 1/2011 | Foley | A61N 7/02 600/411 |
| 2011/0071400 A1 | 3/2011 | Hastings et al. | |
| 2012/0108980 A1 * | 5/2012 | Shilling | A61B 8/0883 600/466 |
| 2013/0123634 A1 * | 5/2013 | Tierney | A61B 8/4281 600/444 |
| 2015/0148667 A1 * | 5/2015 | Mattrey | A61B 8/481 600/424 |

FOREIGN PATENT DOCUMENTS

| | | |
|---|---|---|
| EP | 1780672 A1 | 5/2007 |
| JP | 20110152274 A | 8/2011 |
| JP | 2014-064837 | 4/2014 |
| WO | 9423652 A1 | 10/1994 |
| WO | 9519135 A1 | 7/1995 |
| WO | 9625881 A1 | 8/1996 |
| WO | 9625882 A1 | 8/1996 |
| WO | 9824065 A1 | 6/1998 |
| WO | 9967728 A1 | 12/1999 |
| WO | 2003075770 A1 | 9/2003 |
| WO | 03096872 A2 | 11/2003 |
| WO | 2004032746 A2 | 4/2004 |
| WO | 2005033738 A1 | 4/2005 |
| WO | 2005070300 A1 | 8/2005 |
| WO | 2005071615 A1 | 8/2005 |
| WO | 2005074804 A1 | 8/2005 |
| WO | 2005107623 A2 | 11/2005 |
| WO | 2006042077 A2 | 4/2006 |
| WO | 2006105121 A2 | 10/2006 |
| WO | 2006110830 A2 | 10/2006 |
| WO | 2007041542 A2 | 4/2007 |
| WO | 2007047404 A2 | 4/2007 |
| WO | 2007047566 A2 | 4/2007 |
| WO | 2007109771 A2 | 9/2007 |
| WO | 2008022148 A2 | 2/2008 |
| WO | 2008049084 A2 | 4/2008 |
| WO | 2008107905 A2 | 9/2008 |
| WO | 2009023626 A1 | 2/2009 |
| WO | 2009023801 A1 | 2/2009 |
| WO | 2009121067 A1 | 10/2009 |

OTHER PUBLICATIONS

Watson et al., "Classification of Arterial Plaque by Spectral Analysis of in Vitro Radio Frequency Intra Vascular Ultrasound Data," UltraSound in Med. & Biol., vol. 26 No. I. pp. 73-80, 2000.

McLeod, Andrew L, et al., "Classification of Arterial Plaque by Spectral Analysis in Remodelled Human Atherosclerotic Coronary Arteries," Ultrasound in Med. &. Biol., (2004) vol. 30, No. 2, pp. 155-159.

Official Communication for U.S. Appl. No. 12/563,754 dated Jun. 6, 2012, 43 pages.

Official Communication for U.S. Appl. No. 121563,754 dated Dec. 31, 2012, 11 pages.

Official Communication for U.S. Appl. No. 12/563,754 dated May 22, 2013, 15 pages.

Kawaguchi et al. Usefulness of Virtual Histology Intravascular Ultrasound to Predict Distal Embolization for ST—Segment Elevation Myocardial Infarction, Journal of the American College of Cardiology, vol. 50, No. 17,pp. 1641-1647, 2007.

Caballero, et al. Using Reconstructed IVUS Images for Coronary Plaque Classification, Proceedings of the 29th Annual International Conference of the IEEE EMBS, Aug. 23-26, pp. 2167-2170, 2007.

Sarkar, M. "Modular Pattern Classifiers: A Brief Survey" Systems, Man, and Cybernetics, 2000 IEEE International Conference in Nashville, TN, USA. vol. 4 pp. 2878-2883 (2000).

(56) References Cited

OTHER PUBLICATIONS

Kittler, J. et al., "On Combining Classifiers," IEEE Transactions on Pattern Analysis and Machine Intelligence, Mar. 1998, 20(3):226-239.
Official Communication for U.S. Appl. No. 12/429,005 dated Feb. 14, 2012, 2 pages.
Official Communication for U.S. Appl. No. 12/429,005 dated Apr. 5, 2012, 5 pages.
Official Communication for U.S. Appl. No. 12/429,005 dated Jun. 29, 2012, 26 pages.
Official Communication for U.S. Appl. No. 12/429,005 dated Mar. 21, 2013, 31 pages.
Official Communication for U.S. Appl. No. 12/429,005 dated Nov. 9, 2011, 12 pages.
Official Communication for U.S. Appl. No. 12/429,005 dated Jun. 10, 2011, 10 pages.
International Search Report and Written Opinion for International Application No. PCT/US2016/030573 dated Aug. 4, 2016.

\* cited by examiner

SYSTEMS AND METHODS WITH A SWELLABLE MATERIAL DISPOSED OVER A TRANSDUCER OF AN ULTRASOUND IMAGING SYSTEM

CROSS-REFERENCE TO RELATED APPLICATIONS

This application claims the benefit under 35 U.S.C. § 119(e) of U.S. Provisional Patent Application Ser. No. 62/157,385, filed May 5, 2015, which is incorporated herein by reference.

TECHNICAL FIELD

The present invention is directed to the area of ultrasound imaging systems and methods of making and using the systems. The present invention is also directed to an ultrasound imaging system that includes a transducer disposed within a catheter and a swellable material disposed over the transducer, as well as methods of making and using the ultrasound systems, catheter, and transducer.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical signals that are delivered to the one or more transducers and transformed to acoustic signals that are transmitted through patient tissue. Reflected signals of the transmitted acoustic signals are absorbed by the one or more transducers and transformed to electric signals. The transformed electric signals are delivered to the image processor and converted to an image displayable on the monitor.

Intracardiac echocardiography ("ICE") is another ultrasound imaging technique with proven capabilities for use in diagnosing intravascular diseases and disorders. ICE uses acoustic signals to image patient tissue. Acoustic signals emitted from an ICE imager disposed in a catheter are reflected from patient tissue and collected and processed by a coupled ICE control module to form an image. ICE imaging systems can be used to image tissue within a heart chamber.

BRIEF SUMMARY

One embodiment is a catheter assembly for an ultrasound system. The catheter assembly includes an elongated catheter configured and arranged for insertion into the cardiovascular system of a patient, the catheter having a distal end, a proximal end, and a longitudinal length. The catheter includes a sheath with a proximal portion and a distal portion and the sheath defines a lumen extending along the sheath from the proximal portion to the distal portion. The catheter assembly also includes an imaging core configured and arranged for inserting into the lumen of the catheter. The imaging core includes an elongated, rotatable driveshaft having a proximal end and a distal end and an imaging device coupled to the distal end of the driveshaft with rotation of the driveshaft causing a corresponding rotation of the imaging device. The imaging device includes at least one transducer configured and arranged for transforming applied electrical signals to acoustic signals and also for transforming received echo signals to electrical signals. The imaging core further includes a swellable material disposed on at least the at least one transducer and configured and arranged to rotate with rotation of the driveshaft and to swell upon exposure to a fluid. In at least some embodiments, the swellable material is swollen.

In at least some embodiments, the swellable material is configured and arranged to swell upon exposure to at least one of water, saline, or blood. In at least some embodiments, the swellable material is a hydrogel. In at least some embodiments, the swellable material is configured and arranged to swell and fill a space immediately between the transducer and the sheath so that acoustic signals from the transducer pass from the transducer through the swellable material and directly into the sheath. In at least some embodiments, the swellable material is configured and arranged to swell and fill at least 90% of a space immediately between the transducer and the sheath. In at least some embodiments, the swellable material is mechanically or chemically attached to the imaging core. In at least some embodiments, the swellable material, when swollen, is lubricious.

In at least some embodiments, the catheter assembly further includes a drive unit coupled to the driveshaft, the drive unit configured and arranged for controlling rotation of the driveshaft. In at least some embodiments, the catheter assembly further includes a control module coupled to the imaging core, the control module including a pulse generator electrically coupled to the imaging core, the pulse generator configured and arranged for providing electrical signals to the at least one transducer, and a processor electrically coupled to the imaging core, the processor configured and arranged for processing received electrical signals from the at least one transducer to form at least one image.

Another embodiment is an imaging device that includes at least one transducer configured and arranged for transforming applied electrical signals to acoustic signals and also for transforming received echo signals to electrical signals, and a swellable material disposed on the at least one transducer. In at least some embodiments, the swellable material is swollen.

In at least some embodiments, the swellable material is configured and arranged to swell upon exposure to at least one of water, saline, or blood. In at least some embodiments, the swellable material is a hydrogel. In at least some embodiments, the swellable material is mechanically or chemically attached to the at least one transducer.

A further embodiment is a method of forming any of the catheter assemblies or imaging devices described above. The method includes providing the at least one transducer; and disposing the swellable material on at least the at least one transducer or the imaging core.

In at least some embodiments, disposing the swellable material on the at least one transducer includes coating the at least one transducer with the swellable material or a precursor of the swellable material. In at least some embodiments, the method also includes crosslinking or curing the swellable material or the precursor of the swellable material to mechanically or chemically couple the swellable material to the at least one transducer or the imaging core.

Yet another embodiment is a method of using any of the catheter assemblies described above. The method includes inserting the imaging core into the sheath of the catheter; exposing the swellable material to the fluid causing the swellable material to swell within the sheath; and rotating the driveshaft with the swellable material swollen within the sheath.

In at least some embodiments, exposing the swellable material to the fluid includes injecting water or saline into the sheath of the catheter. In at least some embodiments, exposing the swellable material to the fluid includes allowing blood to flow into the sheath of the catheter. In at least some embodiments, exposing the swellable material to the fluid includes swelling the swellable material to fill a space immediately between the transducer and the sheath so that acoustic signals from the transducer pass from the transducer through the swellable material and directly into the sheath.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of ultrasound imaging systems and methods of making and using the systems. The present invention is also directed to an ultrasound imaging system that includes a transducer disposed within a catheter and a swellable material disposed over the transducer, as well as methods of making and using the ultrasound systems, catheter, and transducer.

Suitable ultrasound imaging systems utilizing catheters include, for example, intravascular ultrasound ("IVUS") and intracardiac echocardiography ("ICE") systems. These systems may include one or more transducers disposed on a distal end of a catheter configured and arranged for percutaneous insertion into a patient. Examples of IVUS imaging systems with catheters are found in, for example, U.S. Pat. Nos. 6,945,938; 7,246,959; and 7,306.561; as well as U.S. Patent Application Publication Nos. 2006/0100522; 2006/0106320; 2006/0173350; 2006/0253028; 2007/0016054; and 2007/0038111; all of which are incorporated herein by reference.

Figure 1:
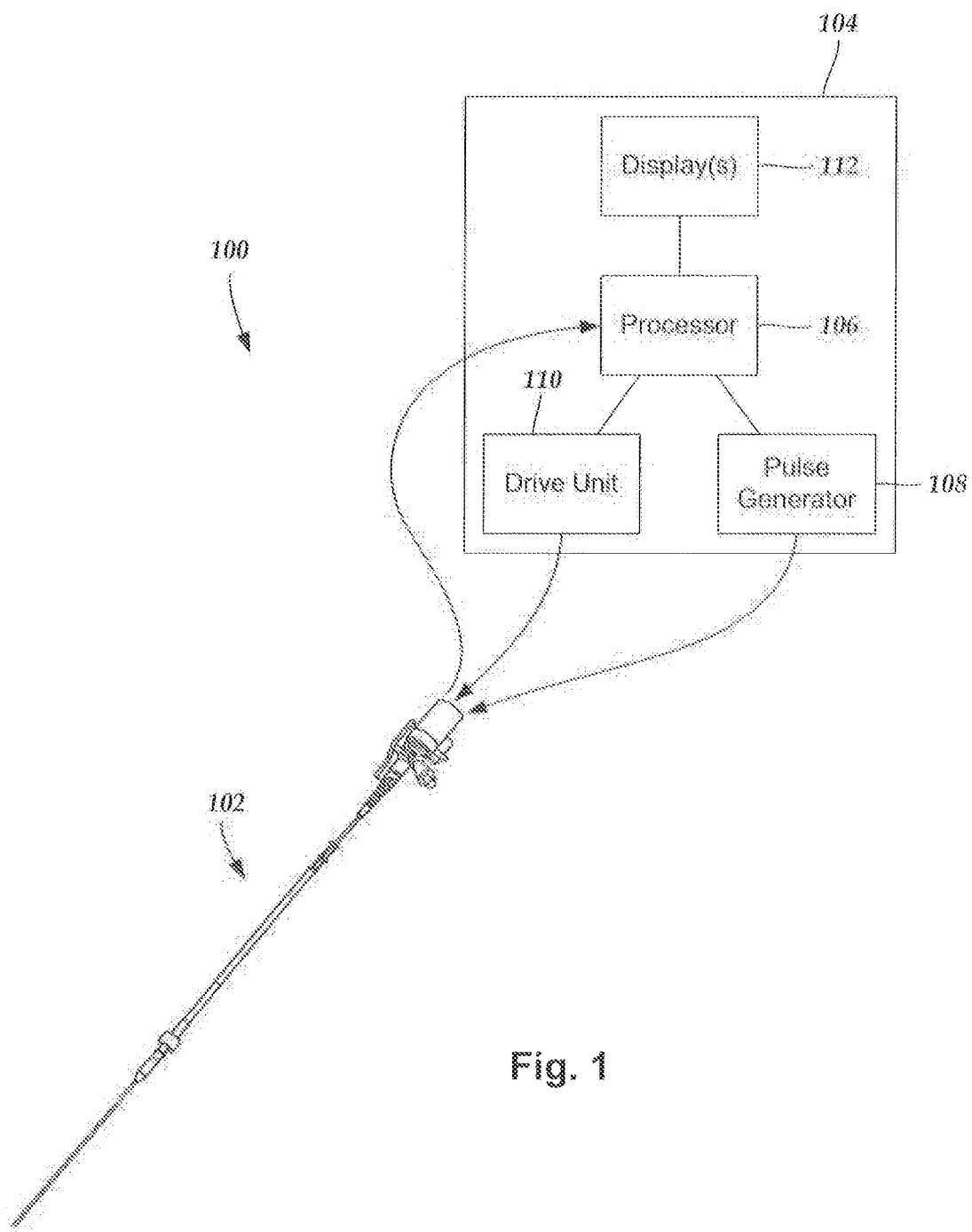
FIG. 1 is a schematic view of one embodiment of an intravascular ultrasound imaging system, according to the invention.

FIG. 1 illustrates schematically one embodiment of an IVUS imaging system 100. An ICE imaging system is similar. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric signals that may be input to one or more transducers (312 in FIG. 3) disposed in the catheter 102. In at least some embodiments, mechanical energy from the drive unit 110 may be used to drive an imaging core (306 in FIG. 3) disposed in the catheter 102.

In at least some embodiments, electrical signals transmitted from the one or more transducers (312 in FIG. 3) may be input to the processor 106 for processing. In at least some embodiments, the processed electrical signals from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical signals transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
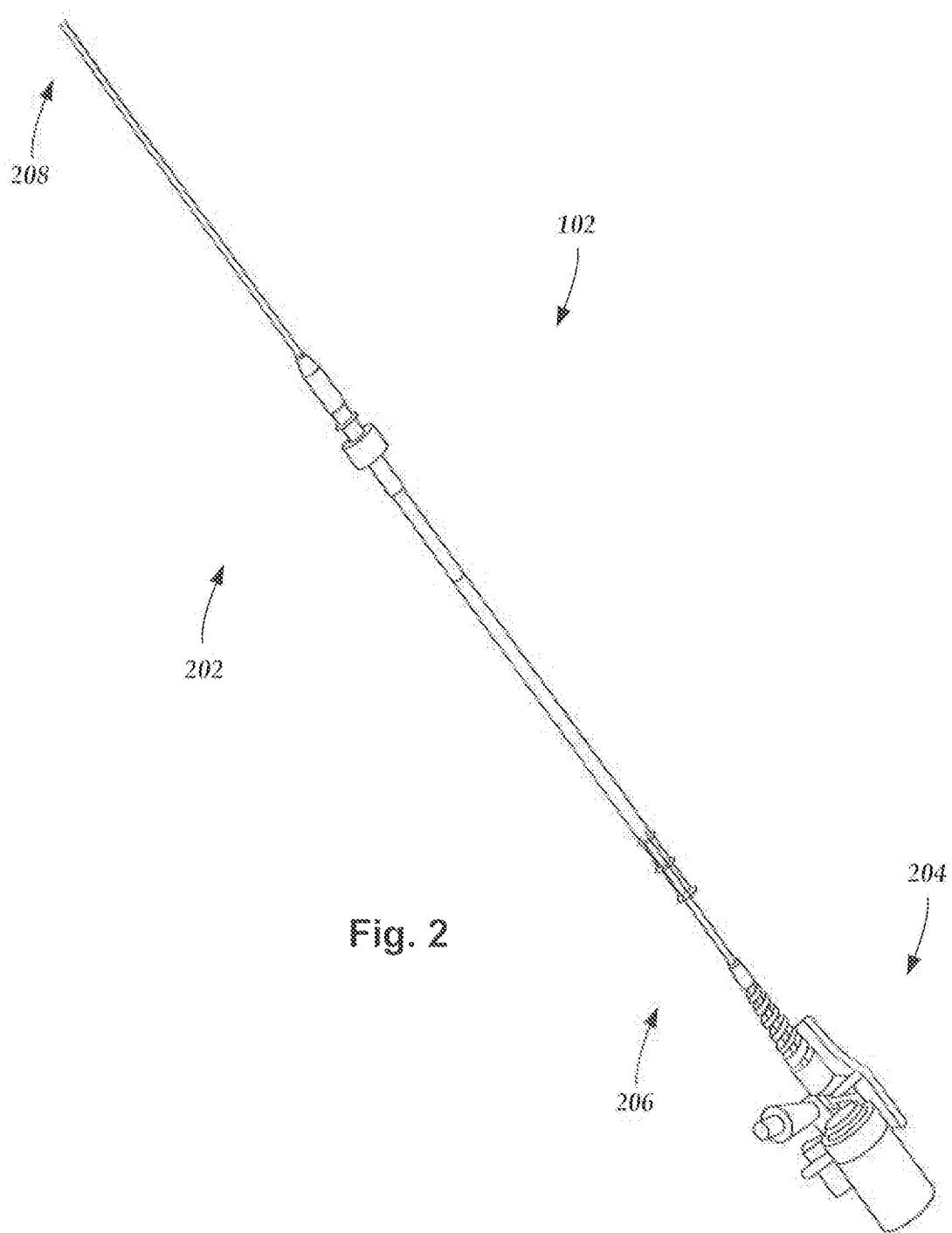
FIG. 2 is a schematic side view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In some embodiments, the elongated member 202 and the hub 204 are formed as a unitary body. In other embodiments, the elongated member 202 and the catheter hub 204 are formed separately and subsequently assembled together.

Figure 3:
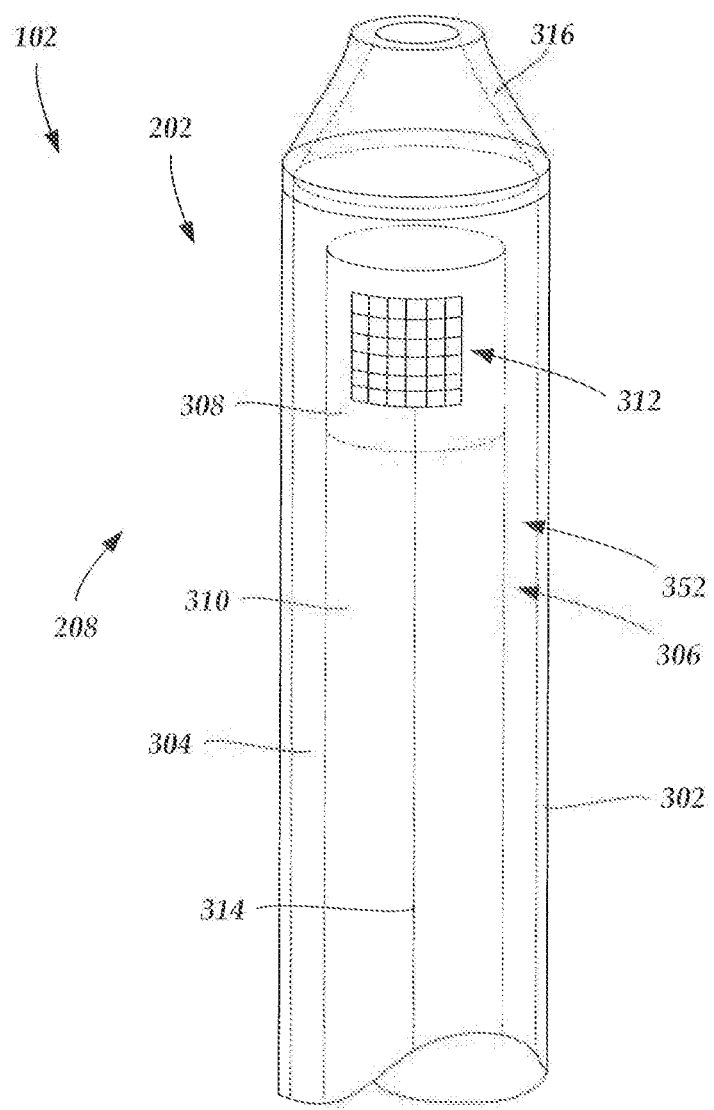
FIG. 3 is a schematic perspective view of one embodiment of a distal end of the catheter shown in FIG. 2 with an imaging core disposed in a lumen defined in the catheter, according to the invention.

FIG. 3 is a schematic perspective view of one embodiment of the distal end 208 of the catheter 102. The catheter 102 includes a sheath 302 having a distal portion 352 and a proximal portion (not shown). The sheath 302 defines a lumen 304 extending along the sheath. An imaging core 306 is disposed in the lumen 304. The imaging core 306 includes an imaging device 308 coupled to a distal end of a driveshaft 310.

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device 308 and employed to transmit and receive acoustic signals. In a preferred embodiment (as shown in FIG. 3), an array of transducers 312 are mounted to the imaging device 308. In other embodiments, a single transducer may be employed. In at least some embodiments, multiple transducers in an irregular-array may be employed. Any number of transducers 312 can be used. For example, there can be one, two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical signals into pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic signals of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic signals of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form a composite image of the walls of the blood vessel and tissue surrounding the blood vessel by stitching together a plurality of individual image frames.

The imaging core 306 is rotated about a longitudinal axis of the catheter 102 while being disposed in the distal portion 352 of the sheath 302. As the imaging core 306 rotates, the one or more transducers 312 emit acoustic signal in different radial directions. When an emitted acoustic signal with sufficient energy encounters one or more medium boundaries, such as one or more tissue boundaries, a portion of the emitted acoustic signal is reflected back to the emitting transducer as an echo signal. Each echo signal that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to generate a displayable image frame of the imaged region based, at least in part, on a collection of information from each of the acoustic signals transmitted and the echo signals received. In at least some embodiments, the rotation of the one or more transducers 312 is driven by the drive unit 110 disposed in the control module (104 in FIG. 1), via the driveshaft 310 extending along the sheath 302 of the catheter 102.

As the one or more transducers 312 rotate about the longitudinal axis of the catheter 102 emitting acoustic signals, a plurality of image frames are formed that collectively form a composite radial cross-sectional image of a portion of the region surrounding the one or more transducers 312, such as the walls of a blood vessel of interest and the tissue surrounding the blood vessel. In at least some embodiments, one or more of the image frames can be displayed on the one or more displays 112. In at least some embodiments, the radial cross-sectional composite image can be displayed on the one or more displays 112.

In at least some embodiments, the imaging core 306 may also move longitudinally (i.e., translate) along the blood vessel within which the catheter 102 is inserted so that a plurality of composite cross-sectional images may be formed into one or more larger composite images that include an axial length of the blood vessel. In at least some embodiments, during an imaging procedure the one or more transducers 312 may be retracted (i.e., pulled back) along the longitudinal length of the catheter 102. In at least some embodiments, the catheter 102 includes at least one section that can be retracted during pullback of the one or more transducers 312. In at least some embodiments, the drive unit 110 drives the pullback of the imaging core 306 within the catheter 102. In at least some embodiments, the drive unit 110 pullback distance of the imaging core is at least 5 cm, 10 cm, 15 cm, 20 cm, 25 cm or more. In at least some embodiments, the catheter 102 pullback occurs along one or more telescoping sections.

The quality of imaging at different depths from the one or more transducers 312 may be affected by one or more factors including, for example, bandwidth, transducer focus, beam pattern, as well as the frequency of the acoustic signal. The frequency of the acoustic signal output from the one or more transducers 312 may also affect the penetration depth of the acoustic signal output from the one or more transducers 312. In general, as the frequency of an acoustic signal is lowered, the depth of the penetration of the acoustic signal within patient tissue increases. In at least some embodiments, the IVUS imaging system 100 operates within a frequency range of 5 MHz to 60 MHz.

One or more transducer conductors 314 electrically couple the transducers 312 to the control module 104 (See FIG. 1). In at least some embodiments, the one or more transducer conductors 314 extend along the driveshaft 310.

The imaging device 308 is inserted in the lumen of the catheter 102. In at least some embodiments, the catheter 102 (and imaging device 308) may be inserted percutaneously into a patient via an accessible blood vessel, such as the femoral artery or vein, at a site remote from a target imaging location. The catheter 102 may then be advanced through patient vasculature to the target imaging location, such as a portion of a selected blood vessel (e.g., a peripheral blood vessel, a coronary blood vessel, or other blood vessel), or one or more chambers of the patient's heart.

Acoustic signals propagating from the one or more transducers propagate through a portion of the lumen surrounding the imaging device before passing through the sheath to the region exterior of the catheter such as a blood vessel or a chamber of a heart. Likewise, echo signals reflected back to the one or more transducers from medium boundaries also propagate through a portion of the lumen. Typically, air is not a desirable transmission medium and image quality may, consequently, be reduced when acoustic signals or echo signals are required by catheter design to propagate through air. In the MHz range, acoustic signals may not propagate at all through air. Accordingly, it is typically advantageous, and in some cases necessary, to purge air from the lumen surrounding the one or more transducers prior to (or one or more times during) the performance of an imaging procedure.

One technique for purging air surrounding the one or more transducers is to flush the lumen with an acoustically-favorable medium, such as water or saline, through which acoustic signals more easily propagate than through air. When using a conventional IVUS imaging system, a lumen of a catheter can be manually flushed to remove air at the beginning of an IVUS imaging procedure. Additionally, the lumen of the catheter may also be manually flushed of air one or more additional times during the course of the IVUS imaging procedure. Unfortunately, each manual flushing of air from the catheter lumen can add to the amount of time it takes to perform an IVUS imaging procedure on a patient.

To reduce the need for repeated flushing during an imaging procedure, a swellable material can be disposed on the transducer. When exposed to fluid, such as water or saline, during, for example, preparation of the catheter for the imaging procedure, the swellable material swells to fill the space between the transducer and the sheath. This can provide an acoustically favorable transmission medium between the transducer and the sheath while eliminating or reducing air bubbles. In at least some embodiments, after the initial swelling of the swellable material there is no need during an imaging procedure to flush the catheter. Alternatively, additional fluid may be added during the imaging procedure to ensure that the swellable material remains swollen. In at least some embodiments, the swellable material is already swollen prior to beginning the imaging procedure or during preparation for the imaging procedure.

Figure 4A:
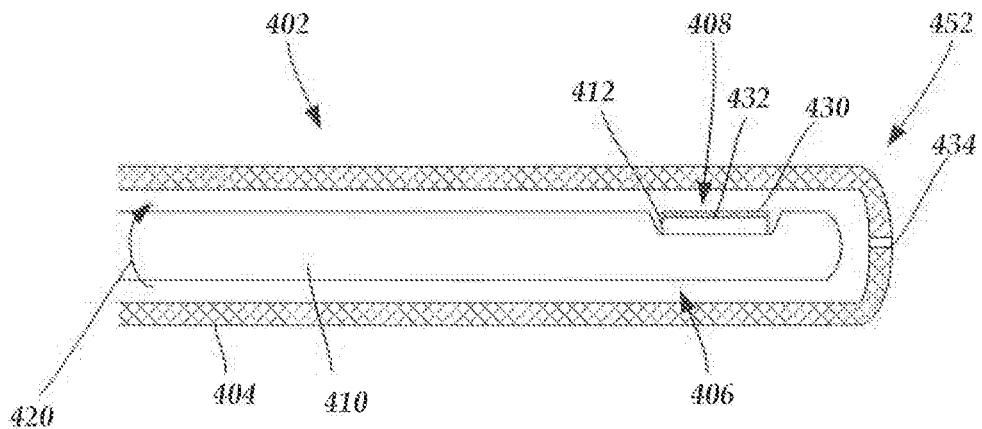
FIG. 4A is a schematic longitudinal cross-sectional view of one embodiment of the distal end of the catheter of FIG. 3 with a swellable material, prior to swelling, disposed over the transducer, according to the invention.
Figure 4B:
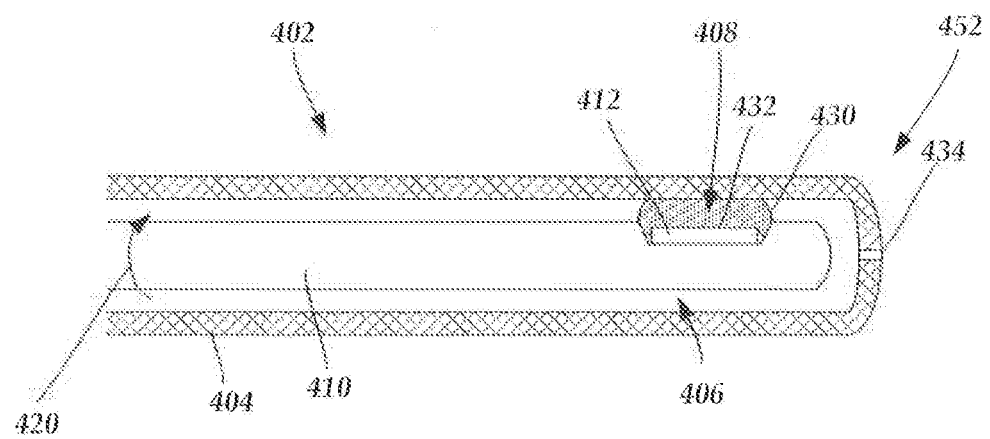
FIG. 4B is a schematic longitudinal cross-sectional view of the embodiment of FIG. 4A with the swellable material, after swelling, disposed over the transducer, according to the invention.
Figure 5A:
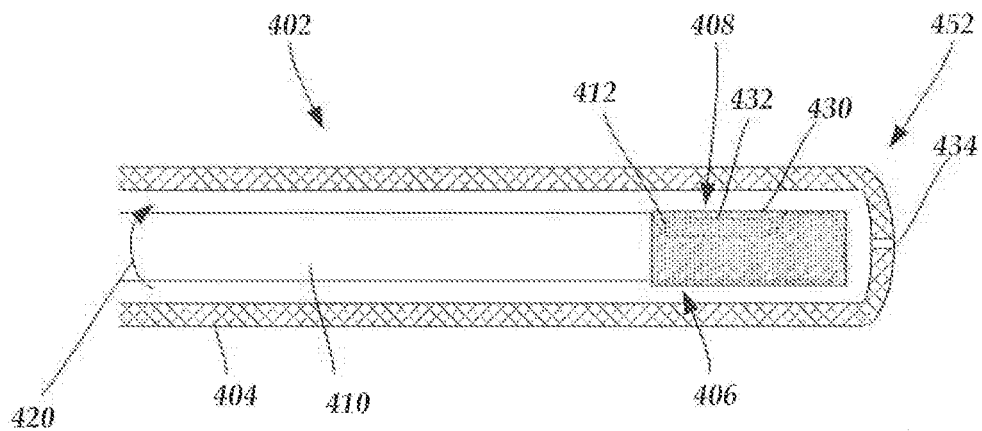
FIG. 5A is a schematic longitudinal cross-sectional view of a second embodiment of the distal end of the catheter of FIG. 3 with a swellable material, prior to swelling, disposed over the transducer and imaging core, according to the invention.
Figure 5B:
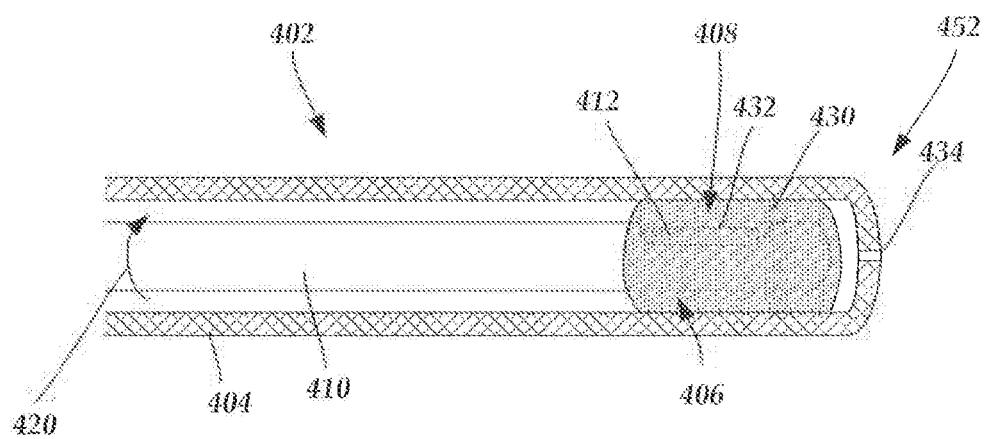
FIG. 5B is a schematic longitudinal cross-sectional view of the embodiment of FIG. 5A with the swellable material, after swelling, disposed over the transducer and imaging core, according to the invention.

FIGS. 4A and 4B are schematic longitudinal cross-sectional views of one embodiment of a distal end 452 of a catheter 402. FIGS. 5A and 5B illustrate a second embodiment of a distal end 452 of a catheter 402. In both embodiments, the catheter 402 includes a sheath 404 and a lumen 406 with an optional flush port 434. In both embodiments, the imaging core 408 is shown disposed in the lumen 406 of the sheath 404 at a distal portion 452 of the sheath 404. The imaging core 408 includes a rotatable driveshaft 410 with one or more transducers 412 coupled to a distal end of the driveshaft 410. The rotatable driveshaft 410 rotates the one or more transducers as illustrated by arrow 420.

A swellable material 430 is disposed on at least the one or more transducers 412. FIGS. 4A and 5A illustrate the swellable material 430 prior to swelling and FIGS. 4B and 5B illustrates the swellable material 430 after swelling. The swellable material 430 in the embodiment of FIGS. 4A and 4B is disposed on at least the acoustically active surface 432 of the one or more transducer 412 from which acoustic signals are emitted and received. In the embodiment of FIGS. 5A and 5B, the swellable material 430 is disposed over a portion of the imaging core 408 including the one or more transducers 412 and extending around the entire circumference of the core and may even extend over the distal end of the imaging core. It will be understood that other variations of the coverage of the swellable material 430 over the imaging core intermediate between the two illustrated embodiments can also be used, as well as variations where the swellable material extends further proximally or distally from the regions in the illustrated embodiments. Preferably, the swellable material 430 is disposed over at least the acoustically active surface 432 of the one or more transducer 412 and may extend over more of the imaging core 408 and further along the lumen 406 of the sheath 404.

In at least some embodiments, the swellable material 430 rotates, even when swollen, with the one or more transducers 412 upon rotation of the driveshaft 410. In some embodiments, a swellable material 430 is selected so that the swellable material, when swollen, forms a lubricious surface that facilitates rotation of the swellable material against the inner surface of the sheath 404. In at least some embodiments, the swellable material 430, when swollen, maintains structural integrity formed in the shape of the catheter lumen 406.

The swellable material 430 can be swollen using a fluid such as, for example, water, saline, or blood. In at least some embodiments, the fluid enters the catheter 402 during a flushing or other procedure. Alternatively or additionally, a fluid, such as blood, can enter the catheter 402 through flush port 434 or other port to swell the swellable material 430. In at least some embodiments, the swellable material 430 is swollen during manufacture and remains swollen thereafter.

As the swellable material 430 swells, the material displaces air bubbles within the lumen 406 of the catheter 402. Preferably, when the swellable material 430 is swollen, the material contacts the inner wall of the sheath 404. In other embodiments, the swellable material 430 fills at least 50%, 66%, 75%, 80%, 90%, 95%, or 99% of the space between the sheath 404 and the acoustically active surface 432 of the one or more transducer 412.

Any suitable swellable material can be used including, but not limited to, hydrogels which are often a hydrophilic network of polymer chains. Often, the polymer chains of a hydrogel are crosslinked, cured, or otherwise arranged to form the network. For example, a hydrogel can include covalent crosslinking between polymer chains, coordinate bonding between polymer chains and inorganic particles, or the like, or any combination thereof. Examples of suitable hydrogels include, but are not limited to, polyvinyl alcohol, acrylamide nano-composite hydrogel, polyvinylpyrrolidone hydrogel, or the like. A nano-composite hydrogel is a polymeric network reinforced with nanoparticles. Preferably, the swellable material is biocompatible for at least the length of time that the catheter is expected to be in contact with patient tissue (for example, at least 1, 2, 4, 8, 12, or 24 hours). In at least some embodiments, the swellable material is acoustically transparent.

In at least some embodiments, the swellable material 430, or one or more precursors of the swellable material, are coated, or otherwise disposed, onto the transducer 412 (for example, on the acoustically active surface 432) and then cross-linked or cured to mechanically or chemically adhere the swellable material to the transducer.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of using a catheter assembly, the method comprising:
    providing a catheter assembly comprising
        an elongated catheter configured and arranged for insertion into a cardiovascular system of a patient, the catheter having a distal end, a proximal end, and a longitudinal length, the catheter comprising a sheath with a proximal portion and a distal portion, the sheath defining a lumen extending along the sheath from the proximal portion to the distal portion, and
        an imaging core configured and arranged for inserting into the lumen of the catheter, the imaging core comprising
            an elongated, rotatable driveshaft having a proximal end and a distal end,
            an imaging device coupled to the distal end of the driveshaft with rotation of the driveshaft causing a corresponding rotation of the imaging device, the imaging device comprising at least one transducer configured and arranged for transforming applied electrical signals to acoustic signals and also for transforming received echo signals to electrical signals, and
            a swellable material disposed on at least the at least one transducer and configured and arranged to rotate with rotation of the driveshaft and to swell upon exposure to a fluid;
    inserting the imaging core into the sheath of the catheter;
    exposing the swellable material to the fluid causing the swellable material to swell within the sheath; and
    rotating the driveshaft with the swellable material swollen within the sheath.

2. The method of claim 1, wherein exposing the swellable material to the fluid comprises injecting water or saline into the sheath of the catheter.

3. The method of claim 1, wherein exposing the swellable material to the fluid comprises allowing blood to flow into the sheath of the catheter.

4. The method of claim 1, wherein exposing the swellable material to the fluid comprises swelling the swellable material to fill a space immediately between the at least one transducer and the sheath so that acoustic signals from the at least one transducer pass from the at least one transducer through the swellable material and directly into the sheath.

5. The method of claim 1, wherein the swellable material is mechanically or chemically attached to the imaging core.

6. The method of claim 1, wherein the swellable material, when swollen, is lubricious.

7. The method of claim 1, wherein the swellable material is configured and arranged to swell upon exposure to at least one of water, saline, or blood.

8. The method of claim 1, wherein the swellable material is a hydrogel.

9. The method of claim 1, wherein the swellable material is configured and arranged to swell and fill at least 90% of a space immediately between the at least one transducer and the sheath.

10. The method of claim 1, wherein the catheter assembly further comprises a drive unit coupled to the driveshaft, the drive unit configured and arranged for controlling rotation of the driveshaft.

11. The method of claim 1, wherein the catheter assembly further comprises a control module coupled to the imaging core.

12. The method of claim 11, wherein the control module comprises a pulse generator electrically coupled to the imaging core, the pulse generator configured and arranged for providing electrical signals to the at least one transducer.

13. The method of claim 12, wherein the control module further comprises a processor electrically coupled to the imaging core, the processor configured and arranged for processing received electrical signals from the at least one transducer to form at least one image.

14. The method of claim 1, wherein the swellable material is coated on the at least one transducer.

15. The method of claim 1, wherein the swellable material is crosslinked on the at least one transducer to mechanically or chemically couple the swellable material to the imaging core.

* * * * *